OR  3,999,832

SEARCH ROOM

United States Patent [19]
Schlesinger

SUBSTITUTE FOR MISSING OR

[11] 3,999,832
[45] Dec. 28, 1976

[54] OPTICAL BEAM EXPANDER AND DIRECTOR CONFIGURATION COELOSCOPE

[75] Inventor: Eugene R. Schlesinger, Wilton, Conn.

[73] Assignee: The United States of America as represented by the Secretary of the Army, Washington, D.C.

[22] Filed: July 11, 1975

[21] Appl. No.: 594,979

[52] U.S. Cl. .................................. 350/6; 350/294
[51] Int. Cl.² ............................................ G02B 27/17
[58] Field of Search ............ 350/6, 7, 294, 22, 25, 350/26, 27, 299, 293, 52, 55, 285, 289, 293; 250/234, 235, 236, 203 R; 244/3.16; 178/7.6; 331/94.5 K

[56] References Cited
UNITED STATES PATENTS 3,907,408   9/1975   Engel .................................. 350/294
3,917,381   11/1975  Feigin ................................. 350/294

Primary Examiner—John K. Corbin
Assistant Examiner—Jon W. Henry
Attorney, Agent, or Firm—Nathan Edelberg; Robert P. Gibson; Charles R. Carter

[57] ABSTRACT

A coeloscope beam expansion and direction system for high energy lasers wherein the system utilizes a cassegrain telescope folded into a coelostat. The beam expander optics are placed between the azimuth axis gimbal and the elevation axis gimbal rather than at the output of the optical train as in the telescope concept or at the input of the optical train as in the coelostat concept.

4 Claims, 1 Drawing Figure

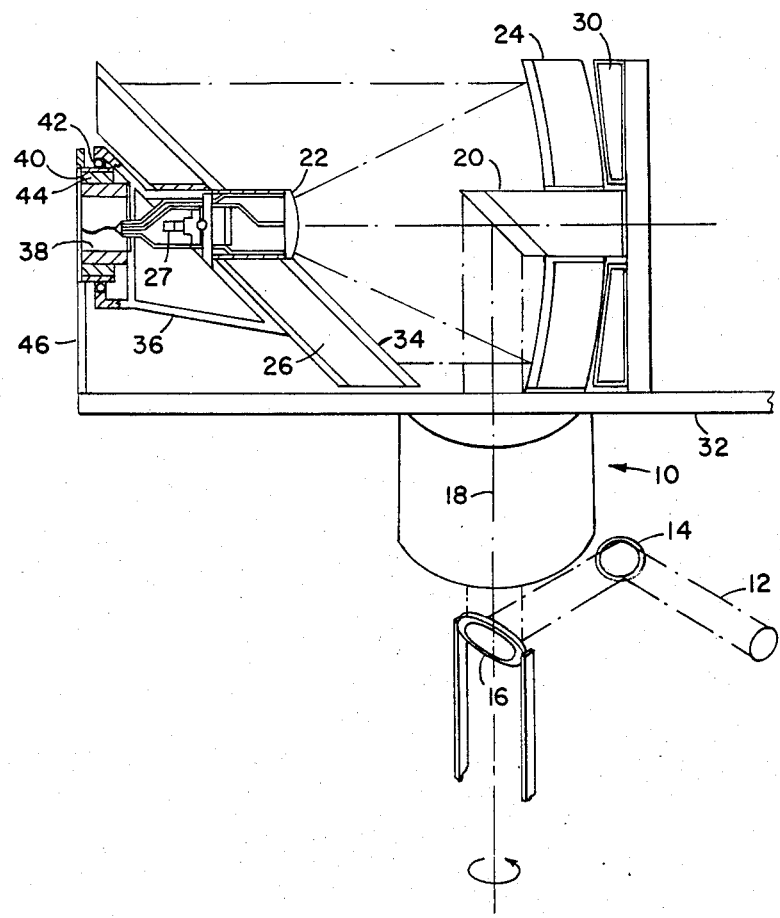

OPTICAL BEAM EXPANDER AND DIRECTOR CONFIGURATION COELOSCOPE

DEDICATORY CLAUSE

The invention described herein was made in the course of or under a contract or subcontract thereunder with the Government and may be manufactured, used, and licensed by or for the Government for governmental purposes without the payment to me of any royalties thereon.

BACKGROUND OF THE INVENTION

This invention relates to the field of optical beam expanders. Coupling of an unexpanded laser beam from a fixed source to a controlled direction after expansion when accomplished by conventional gimballed telescopes necessitates the use of many mirrors to couple the unexpanded beam across rotational axes. This arrangement involves a problem of cooling the secondary mirror supporting structure that is illuminated by the exiting beam where relatively high optical power levels prevail. Another undesirable feature is that the undue susceptibility to wind loads can cause telescope mispointing. When coupling an expanded laser beam by a conventional coelostat arrangement the direction of the beam is accomplished by the use of two large mirrors at the output end of the optical train. These mirrors are moved together about the azimuth axis to obtain one motional degree of freedom. The other degree of freedom is implemented by controlled motions of one mirror about the elevation axis. A disadvantage of the coelostat arrangement is that a relatively large sweep volume is required.

SUMMARY OF THE INVENTION

The present invention has provided a solution to such problems by placing the beam expander optics between the azimuth and elevation gimbals. This specific placing allows a more compact optical arrangement for beam expansion with the advantage of fewer mirrors than the telescope concept and less critical elements than the coelostat concept.

This invention may be better understood from the following detailed description taken in conjunction with the accompanying drawing.

BRIEF DESCRIPTION OF THE DRAWING

The single FIGURE shown is a pictoral view of the coeloscope beam expander optics system.

DESCRIPTION OF THE PREFERRED EMBODIMENT

Referring now to the drawing, reference numeral 10 generally indicates the beam expander optics system wherein a laser beam enters the system at 12. The beam is transmitted by a mirror 14 to a transfer mirror 16 which reflects the beam from horizontal to vertical concentric with the azimuth axis 18 about which the system rotates. A beam steering mirror 20 folds the beam to the left along a horizontal axis to hit a secondary convex mirror 22 which expands the beam to one meter at the primary concave mirror 24 at its right. The secondary mirror 22 is mounted in the frame 26 and focus adjustment is provided by a motor drive 27 operating through a differential screw or other suitable drive connection. Primary mirror 24 is mounted to a frame 30 that sits directly on the main structural beam 32 and also supports the beam steering mirror 20 so that the central axis of mirrors 20 and 24 are concentric. The primary mirror 24 reflects an almost parallel beam to the left against a coeloscope flat 34 and thence out into the atmosphere. The support frame 26 for coeloscope flat 34 is rotatably mounted on the outer race of bearing 36 together with the armature of drive means 38. A ring 40 carrying the inner race 42 and motor stator 44 is mounted to the structure 46.

The first degree of motional freedom is obtained by rotating the telescope about the vertical or azimuth axis located concentric to the upward directed unexpanded beam. The second motional degree of freedom can be obtained by (a) rotation of only the coeloscope flat 34 by drive means 38 or (b) rotation of flat 34 and secondary mirror 22. These options make unnecessary the need for a secondary mirror support means which are illuminated by the optical beam.

Thus the coeloscope beam expansion system provides a more compact optical arrangement for beam expansion and direction while employing fewer mirrors than the telescope and smaller and less critical elements than in the coelostat. The coeloscope system is also less sensitive to input beam angle errors since the first gimbal is crossed by the unexpanded beam.

I claim:
1. A coeloscope beam expansion and direction system for use with high energy collimated laser beams comprising: a vertical axis around which said system rotates; means for transferring an incoming unexpanded laser beam concentric with said axis; a steering mirror for folding said beam along a horizontal axis; a mirror for expanding said folded beam; a second mirror disposed on an axis concentric with said steering mirror for receiving said expanded beam and reflecting an almost parallel beam, and a coelostat flat disposed on a support behind said expanding mirror for receiving said collimated beam and folding said beam out into the atmosphere.

2. A coeloscope beam expansion system as set forth in claim 1 wherein said expanding mirror reflecting surface is convex and said second mirror reflecting surface is concave.

3. A coeloscope beam expansion system as set forth in claim 2 wherein said convex mirror is provided with means for adjusting the focus thereof.

4. A coeloscope beam expansion system as set forth in claim 3 wherein said coelostat flat is provided with drive means for rotating said flat.

* * * * *